(12) United States Patent
Abita et al.

(10) Patent No.: US 6,875,196 B2
(45) Date of Patent: Apr. 5, 2005

(54) VESTIBULAR IRRIGATOR TEST SYSTEM (VITS)

(75) Inventors: Joseph L. Abita, Boyds, MD (US); Leonard R. Proctor, Baltimore, MD (US)

(73) Assignee: The Johns Hopkins University, Baltimore, MD (US)

(*) Notice: Subject to any disclaimer, the term of this patent is extended or adjusted under 35 U.S.C. 154(b) by 0 days.

(21) Appl. No.: 10/203,850

(22) PCT Filed: Feb. 16, 2001

(86) PCT No.: PCT/US01/05093
§ 371 (c)(1),
(2), (4) Date: Nov. 25, 2002

(87) PCT Pub. No.: WO01/60429
PCT Pub. Date: Aug. 23, 2001

(65) Prior Publication Data
US 2003/0208155 A1 Nov. 6, 2003

Related U.S. Application Data

(60) Provisional application No. 60/183,183, filed on Feb. 17, 2000.

(51) Int. Cl.$^7$ .............................................. A61M 31/00
(52) U.S. Cl. ........................ 604/67; 604/66; 604/890.1
(58) Field of Search .................. 128/DIG. 12, DIG. 13; 607/114; 600/152, 156–159; 604/901, 503, 65, 66, 67, 80, 81, 94.01, 118, 120, 131, 132, 173, 181, 183

(56) References Cited

U.S. PATENT DOCUMENTS

| | | |
|---|---|---|
| 3,000,271 A | 9/1961 | Harvey |
| 3,363,620 A | 1/1968 | Collins |
| 3,563,231 A | 2/1971 | Ducote ........................ 128/2.1 |
| 3,942,515 A | 3/1976 | Servos ........................... 128/2 |
| 4,023,561 A | 5/1977 | Servos ........................ 128/2.1 |
| 4,106,493 A | 8/1978 | Proctor ........................... 128/2 |
| 4,106,496 A | 8/1978 | Proctor ........................... 128/2 |
| 4,143,649 A | 3/1979 | Foti ............................... 128/2 |
| 4,190,033 A | 2/1980 | Foti ............................ 128/742 |
| 4,194,512 A | 3/1980 | Foti ............................ 128/742 |
| 4,244,377 A | 1/1981 | Grams ........................ 128/742 |
| 4,299,237 A | 11/1981 | Foti ............................ 128/742 |
| 4,325,386 A | 4/1982 | Katz ........................... 128/733 |
| 4,830,024 A | 5/1989 | Nashner et al. ............. 128/787 |
| 4,844,074 A | 7/1989 | Kurucz ....................... 128/401 |
| 5,303,715 A | 4/1994 | Nashner et al. ............. 128/782 |
| 6,302,864 B1 * | 10/2001 | Nowosielski ................ 604/65 |

* cited by examiner

*Primary Examiner*—Kevin C. Sirmons
(74) *Attorney, Agent, or Firm*—Benjamin Y. Roca, Esq.

(57) ABSTRACT

The present invention provides automated control of aural irrigation by utilizing a process controller in connection with an irrigation supply unit and irrigation delivery unit. Sensors situated in the irrigation supply unit and irrigation delivery unit provide data feedback to the process controller enabling essentially instantaneous and precise control of operational parameters. In addition, data customized to individual patients as well as historical data for use in analysis is stored in and processed by the control processor to increase the accuracy and utility of the aural irrigation system. Further, patient response data (e.g., from an ENG sensor) is also input to the process controller, thereby enabling extremely fast and accurate test analysis with minimal effort by the device operator.

9 Claims, 4 Drawing Sheets

VESTIBULAR IRRIGATOR TEST SYSTEM (VITS)

CROSS-REFERENCE TO RELATED APPLICATIONS

This application is based on U.S. Provisional Application No. 60/183,183, filed on Feb. 17, 2000, which application is incorporated fully herein by reference.

BACKGROUND OF THE INVENTION

1. Field of the Invention

This invention relates to clinical caloric ear testing, and more particularly to a method and apparatus for automatically coordinating and controlling the operation of a testing and diagnostic apparatus related to clinical caloric ear testing.

2. Description of the Related Art

Human balance disorders are common and they may result in serious and protracted suffering and disability. For example, a patient with Meniere's disease (recurrent aural vertigo) may experience attacks of severe vertigo, nausea and vomiting for years. Finding the specific cause of a patient's balance disorder is key to appropriate treatment. There are different conditions which manifest these symptoms, such as heart irregularities, blood vessel narrowing, brain tumor, and stroke, to name a few. Fairly often the cause originates in the inner ear.

In 1906, Robert Barany introduced a way to test the inner ear's balance reflex using warm or cool water irrigation in the ear canal (the "caloric" test), for which he was awarded a Nobel Prize. No practical method for controlling the intensity of the caloric test (analogous to controlling/setting loudness in hearing tests) was available until, in 1972, Proctor and Dix reported a new technique, the "temperature switching" caloric (TSC) test. In this test, the caloric stimulus intensity acting on the inner ear was controlled by switching the temperature of the caloric irrigation at specific times, in keeping with physical and mathematical models of heat flow in the temporal region about the inner ear. A clinical TSC test system, described in U.S. Pat. No. 4,106,496 to Proctor et al., incorporated fully herein by reference, was subsequently developed for vestibular function diagnosis and is still in use today.

Prior art methods provide for control and adjustment of the alternation between the two temperature fluids by use of an electrical timer, and include temperature sensors in the nozzle of the fluid delivery device which send temperature information to a meter or recorder. However, in the prior art, the processes of adjusting the timing and of inputting testing parameters relative to a particular patient, for example, all must be performed manually by operator input prior to each test. Further, processing of the data resulting from the testing must also be performed manually. Accordingly, it would be desirable to have a method and apparatus which would enable more precise measurement and control and would also allow the storage and retrieval of patient data for use in setting up and adjusting the test procedures and for research purposes.

SUMMARY OF THE INVENTION

The present invention provides automated control of aural irrigation by utilizing a process controller in connection with an irrigation supply unit and irrigation delivery unit. Sensors situated in the irrigation supply unit and irrigation delivery unit provide data feedback to the process controller enabling essentially instantaneous and precise control of operational parameters. In addition, data customized to individual patients as well as historical data for use in analysis is stored in and processed by the control processor to increase the accuracy and utility of the aural irrigation system. Further, patient response data (e.g., from an ENG sensor) is also input to the process controller, thereby enabling extremely fast and accurate test analysis with minimal effort by the device operator.

DESCRIPTION OF THE PREFERRED EMBODIMENT(S)

Figure 1:
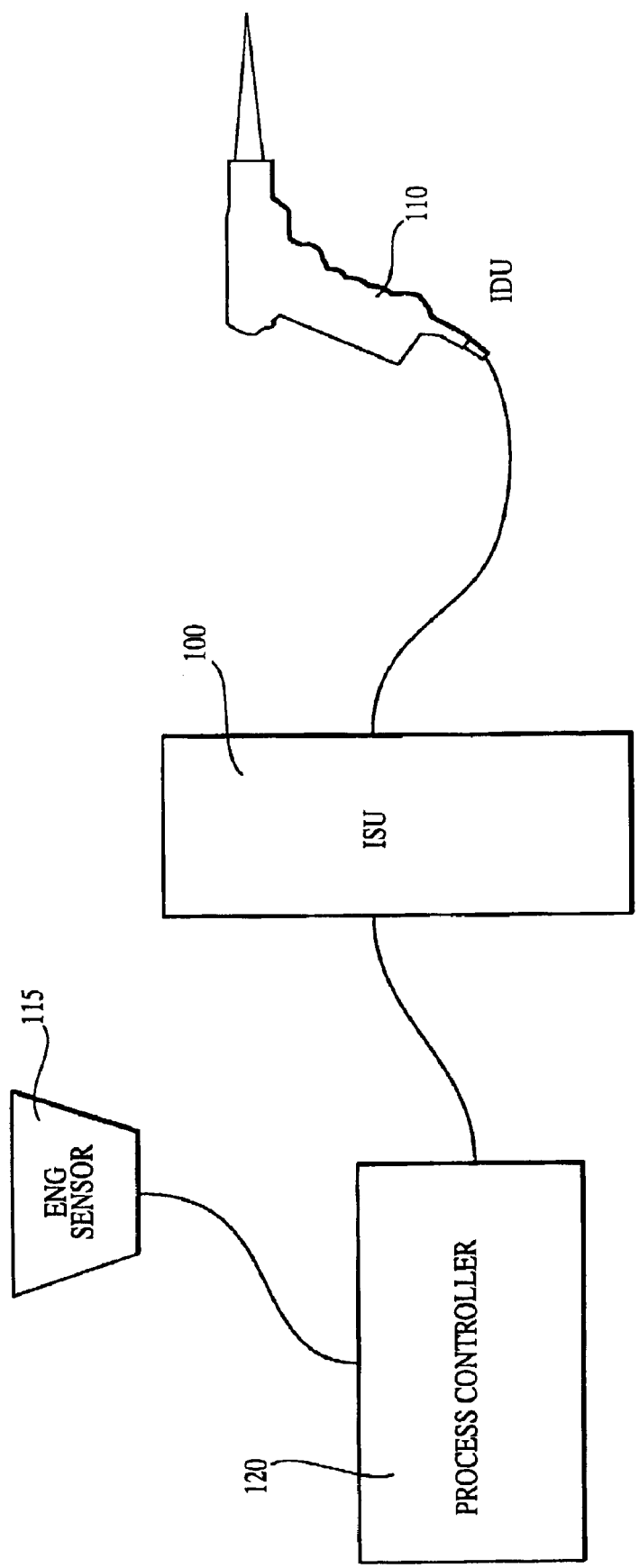
FIG. 1 is a block diagram of the present invention.

FIG. 1 illustrates a block diagram of the present invention. An Irrigation Supply Unit (ISU) 100 for storage of irrigation fluid is coupled to an Irrigation Delivery Unit (IDU) 110, which delivers the irrigation fluid to the patient during a test procedure. The ISU 100 is coupled to process controller 120 that controls signals and data can be exchanged between them. A patient response sensor for measuring the activity of a patient under test, such as a conventional ENG sensor 115, is coupled to process controller 120 to enable the delivery of ENG data (discussed in more detail below) to process controller 120 for analysis and storage.

Process controller 120 is a programmable computing device capable of being configured to control the ISU 100 and IDU 110 to deliver timed pulses of water or other fluid via multiple channels. In a typical operation, the process controller 120 directs the ISU 100 to operate two channels: a "hot" temperature channel which delivers fluid at approximately 44° C. to the IDU 110 and a "cold" temperature channel which delivers fluid at approximately 30° C. to the IDU 110. In a preferred embodiment, the process controller is configured to be able to control the ISU 100 and IDU 110 to deliver a "square wave" water pulse to a patient's aural canal for a duration of up to 100 seconds at a fluid delivery (flow) rate of (up to) 350±50 cc/min. Obviously, the exact rates and temperatures can be varied, depending on the needs of the patient undergoing the test. If desired, the irrigation channels' flow rates can be manually set instead, by overriding the process controller in a conventional manner.

Figure 2:
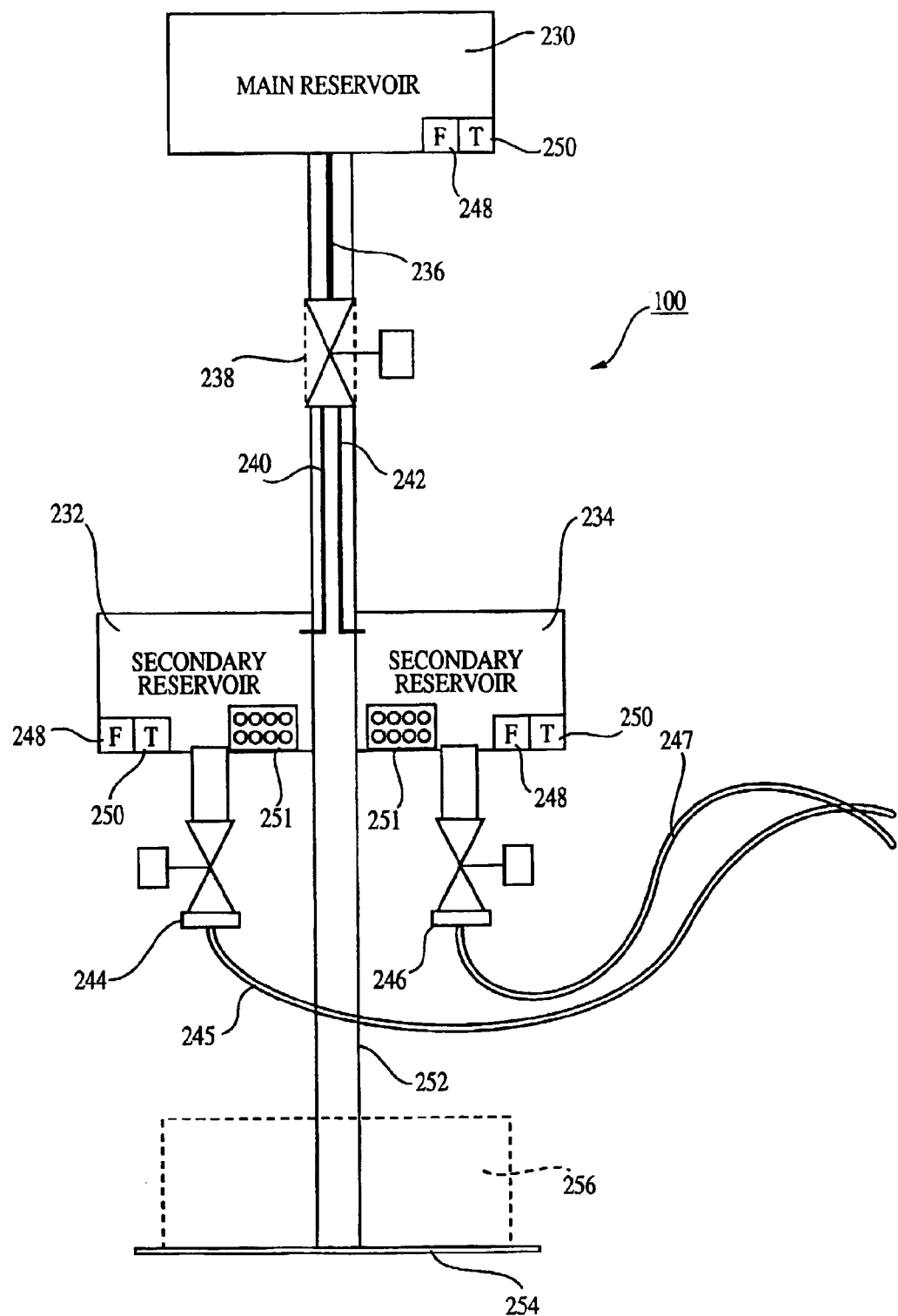
FIG. 2 illustrates a preferred embodiment of an irrigation supply unit 100 of FIG. 1.

FIG. 2 illustrates a preferred embodiment of the ISU 100 in more detail. Referring now to FIGS. 1 and 2, pre-bottled sterilized water is "loaded" into a main fluid reservoir 230 mounted atop a support post 252. A main supply tube 236 extends through support post 252 from main reservoir 230 to a valve 238. In a preferred embodiment, valve 238 is a remotely controllable valve (e.g., motor-controlled or solenoid-driven valve) having a single input and two separately controllable outputs which control the flow of fluids to secondary supply tubes 240 and 242. In a preferred embodiment, control of the operation of valve 238 is performed by process controller 120.

Secondary supply tubes 240 and 242 provide a delivery path to secondary reservoirs 232 and 234, respectively, from main reservoir 230. Secondary reservoir 232 includes a remotely controllable valve 244 which, in a preferred embodiment, under control from process controller 120, automatically regulates the flow of fluid from secondary reservoir 232 to the IDU 110 (not shown in FIG. 2) via delivery tube 245. Similarly, secondary reservoir 234 includes a remotely controllable valve 246 for automatic control of fluid from secondary reservoir 234 to IDU 110 via delivery tube 247.

A base 254 is connected to support post 252 to provide a stable platform for the ISU 100 to be supported upon, and, if desired, an expended fluid reservoir 256 can be provided at base 254 to receive expended fluids used during the irrigation process (flow tubes for delivery of the expended fluids are not shown in this drawing).

In one embodiment, main fluid reservoir 230 is a room temperature source (~17–20° C.) which feeds the two secondary reservoirs 332 and 334 (e.g., ~0.5 ml each) which can, as discussed below, rapidly heat and stabilize their "charge" of water to the desired temperatures, e.g., 44° C. and 30° C., respectively, in this example. The secondary reservoirs 232 and 234 deliver temperature-stabilized water to the IDU 110.

Fluid level sensors 248 and temperature sensors 250 in each of the reservoirs are connected in a known manner to provide feedback to the process controller 120 regarding the amount and temperature of the fluids contained in the reservoirs. Heating coils 251 (or any known controllable heating apparatus) controllable by process controller 120 provide heat to increase the temperature of the fluids in secondary reservoirs 232 and 234. If desired, a heating element can also be provided in main reservoir 230 to preheat the fluid stored therein to a temperature above room temperature but below the lowest secondary reservoir temperature. Although not shown, flow rate sensors may be included, for example, in delivery tubes 245 and 247, to provide fluid flow data to process controller 120.

Based on data returned to the process controller 120 from the sensors, the valves and heaters are controlled by process controller 120 as required to keep the reservoirs filled, control the timing and speed of fluid to the IDU 110, and to maintain the temperature of the fluids at the desired levels. The process controller 120 can be configured to assure that the secondary reservoirs 232 and 234 are filled sufficiently for a complete test at the beginning of each test cycle. Of course, process controller 120 could be configured to provide for continuous refilling of the secondary reservoirs 232 and 234 during the test process, to trigger alarms to indicate low fluid and/or fluid temperature levels, to trigger alarms or open/close valves when flow rates go above or below a certain threshold, or any other parameters/operations carried out by the ISU 100 and/or IDU 110.

The process controller 120 provides its control function via a computerized "intelligent agent" which is simply a computer program providing operational instructions for the system in keeping with a patient-customized or physician-customized process. The number of immediately sequential, complete tests that can be accomplished by the system is limited only by the ability to keep the secondary reservoirs "refreshed" with fluid following each test. Thus, for example, if the main fluid reservoir 230 were supplied by a constant fluid refill source so that it was automatically refilled upon reaching a predetermined minimum fluid level, the system could operate essentially continuously. Using a "fresh" pre-bottled and sterilized irrigation charge for each patient tested essentially eliminates the potential for water contamination. The irrigation supply is designed for ease of routine operation, sterilization, cleaning, maintenance, and repair.

Each channel's water temperature and flow rate may be constantly monitored and validated automatically by an automatic calibration component (i.e., a monitoring and validation subroutine) of the intelligent agent.

Following is an example of the operation of the present invention to perform a biphasic TSC test. In operation, the physician or clinician performs a bi-phase caloric irrigation by injecting water into a patient's aural canal at a specified temperature, flow rate, and time, all of which are controlled by process controller 120 and the intelligent agent stored therein. Process controller 120 includes memory so that, if desired, test parameters specific to each patient, as well as historical test data, may be stored and recalled whenever desired. This minimizes the amount of operator action required, reducing the risk of errors due to the inputting of incorrect parameters, and freeing up the operator to perform other tasks.

In a typical biphasic test (both biphasic and uniphasic stimulation profiles are embodied in this system), first a hot water (e.g., 43.5° C.) irrigation pulse is injected into the patient's aural canal for a time which creates the desired temperature difference across his or her lateral semicircular canal (e.g., ~40 sec for a $\Delta T$~+0.8° C.). This is followed by a cold water (e.g., 30.5° C.) irrigation pulse into the aural canal to produce a reverse temperature gradient (e.g., ~60 sec for a $\Delta T$~–0.8° C.). A final hot water (e.g., ~43.5° C.) irrigation pulse is then applied to the patient's aural canal to return the lateral semicircular canal to body temperature (~37° C.) equilibrium (e.g., ~12 sec for a $\Delta T$~0° C.). It is understood that each of the test parameters, e.g., temperature, flow rate, duration, etc., may be the same for each patient or may be variable dependent on the test being performed, the particular physical characteristics of the patient, etc.

Nystagmus is a rapid involuntary oscillation of the eyeballs which can be caused by inner ear disorders, such as Meniere's disease, and caloric testing also triggers nystagmus. This triggering of nystagmus by caloric testing is monitored by physicians to assess the performance of the patient's balance control receptors. Conventionally, a process known as electro-nystamography (ENG) is used to measure and record a patient's nystagmus during caloric testing. In accordance with the present invention, the patient's recorded ENG responses (sensed by ENG sensor 115 of FIG. 1) are input and stored in the process controller 120; the ENG data is subsequently analyzed in a well-known manner by the process controller 120 using conventional analysis techniques to diagnose the performance of the patient's balance control system receptors.

The present invention can work together with the ENG as set forth above, or with other instruments such as an EEG, in an interactive mode, for patient calibration, testing, and diagnosis (real-time). The signals of, for example, the ENG, would be monitored within the VIS and changes to the process would be made in real-time as the test is conducted.

In a preferred embodiment, the IDU 110 comprises a hand-held instrument with a "trigger" to start or cancel the process described above. A nozzle permits the practitioner to position and direct the irrigation stream within the aural canal as required by a patient's orientation and anatomical features. Included in the IDU 110 are point-of-delivery sensors and point-of-delivery heaters (not shown) that enable temperature sensing and temperature adjustments of the fluid streams at the point of delivery. Thus, the temperature of the fluid stored in the secondary reservoirs 232 and 234 need only be close to (slightly lower than) the temperature of the fluid to be delivered at the patient's aural canal. The IDU's point-of-delivery sensors send data relating to the sensed temperature to the process controller 120, where a determination is made as to whether the water is within a predetermined temperature range set by the patient's statistical information or set manually by an operator of the device. The process controller 120 is configured to activate the point-of-delivery heaters, if needed, to increase the temperature of the fluid being delivered. Thus, the present invention avoids complications associated with having to maintain precisely accurate temperatures of the primary and secondary reservoirs. Further, the need to maintain fluid temperatures constant during travel from the reservoir to the IDU 110 (e.g., over the source-to-patient delivery tube length typical of a clinical setting) is eliminated.

Although not shown, if desired a variable (e.g., sharp to diffuse) focus illuminator may be provided in the IDU 110 near the nozzle (or alternatively in the nozzle) to assist the clinician in viewing the area in which they are working. It is not unusual for caloric testing to be performed in darkened conditions; accordingly, if desired, the illumination performed by the variable focus illuminator could be performed with the use of infrared and conventional night-vision apparatus to assist the clinician in seeing in darkened conditions.

The present invention also allows the obtaining of a specified dynamic temperature profile at the point of delivery for both the hot and cold channels. Among other things, the ability to measure and store dynamic temperature profiles at the point of delivery will allow the application of irrigation at different parametric settings, and enable correlation of the effects with models. By obtaining statistical data results from individuals and from different populations, models can be refined and customized to individuals and populations. An acceptable accuracy for water temperature profiles is ±0.2° C. This is consistent with the minimum profile temperature being the secondary reservoirs' nominal temperature and the maximum profile temperature not exceeding $T_{channel}+3°$ C., not to exceed a temperature inconsistent with patient comfort at the point of delivery.

The intelligent agent in concert with the process controller 120 automatically ascertains patient test requirements, determines and customizes the process parameters for a particular patient, initializes the ISU parameters prior to start-up, and controls all aspects of the actual test procedure. During the test, the process controller 120 collects ENG, process, patient and other data; and, subsequently, performs analysis, yields information in desired formats, assists diagnosis, gives statistical and trend indications, and archives patient data and records. The specific analysis, diagnostics, and data/results formatting calculations are performed using conventional techniques and such techniques themselves are not considered novel, per se.

Figure 3:
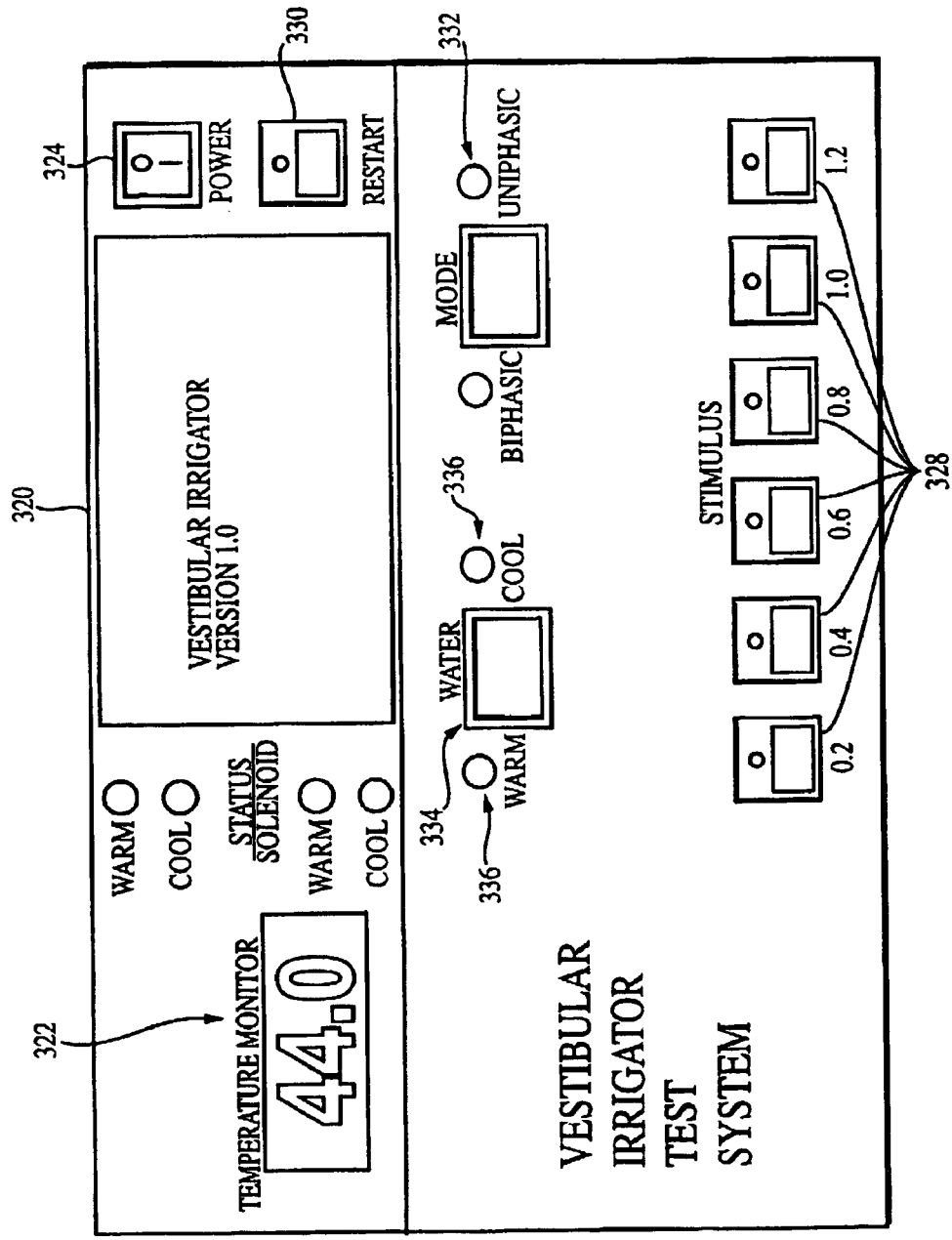
FIG. 3 illustrates an example of a dedicated process controller in accordance with the present invention.

Process controller 120 can comprise a personal computer, mainframe computer, or any known processing device. In a preferred embodiment, an example of which is illustrated in FIG. 3, process controller 120 comprises a dedicated processor unit 320 including, for example, relevant displays (e.g., temperature displays 322, flow rate displays, etc.), specific controlling components (e.g., power switch 324), preset stimulus selection switches 328 for selecting, e.g., stimulus levels; a "restart" button 330; mode selector 332 (e.g., for selecting between a biphasic and uniphasic mode); a fluid temperature selector 334 with LED's 335 to indicate which reservoir is selected; valve status LED indicators, etc. Specific components for performing the control and display functions are well known in the art.

Figure 4:
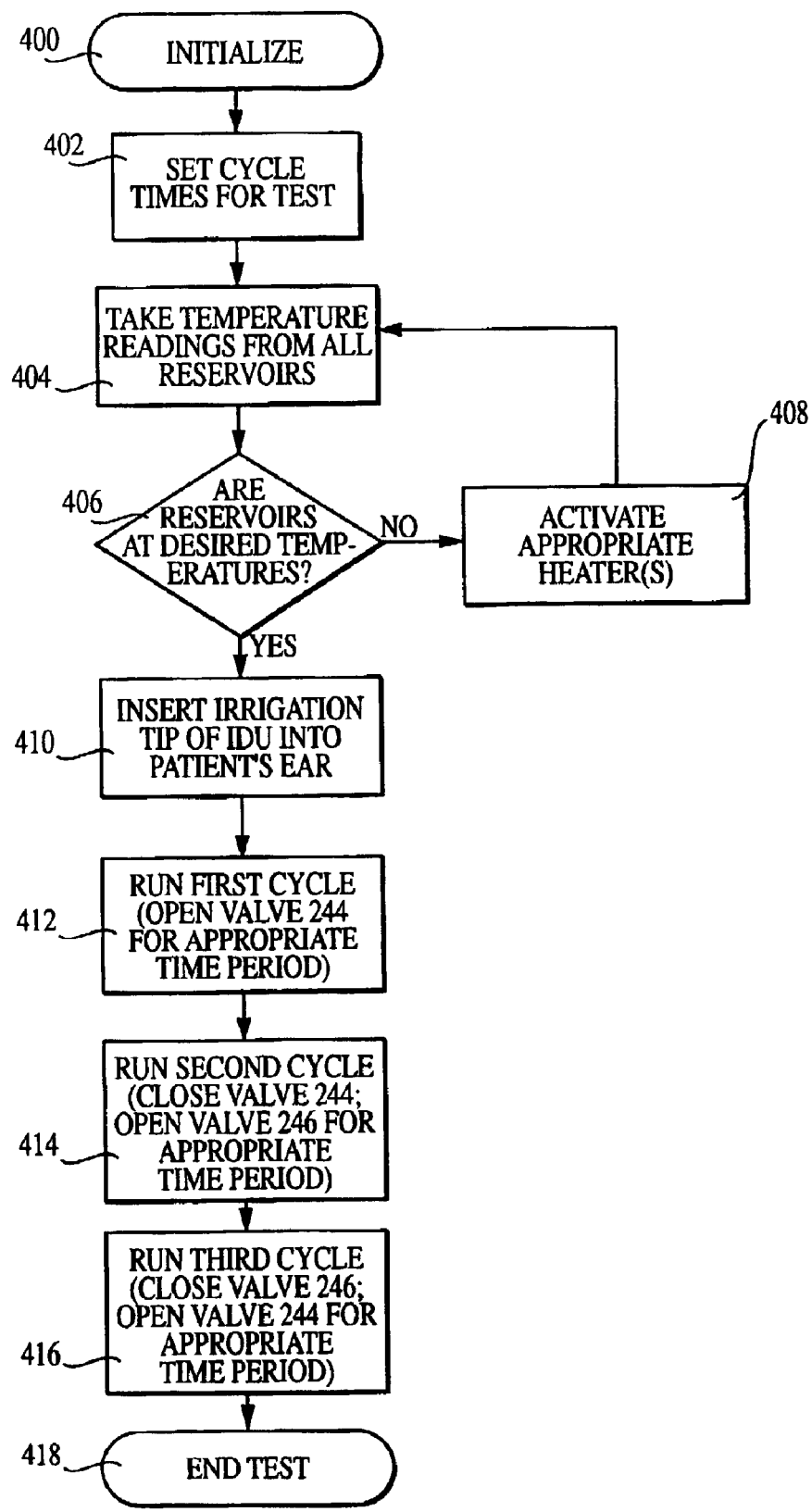
FIG. 4 is a flowchart illustrating the basic steps performed in accordance with the present invention.

FIG. 4 is a flowchart illustrating an example of steps performed by the present invention during a typical test. At step 400, the system is initialized. Initialization essentially comprises the steps required to set up the system for a test operation. For example, during the initialization step, the fill sensors 248 determine the fill level of each of the reservoirs. If the reservoirs are not properly filled, alarms may be activated and/or valve 238 can be opened until secondary reservoirs 232 and 234 are filled to the appropriate level. In addition, readings are taken from temperature sensors 250 to make sure that various temperatures are at the appropriate levels. If the temperatures are below the appropriate initialization levels, then heaters 251 are activated until the temperature stabilizes at the desired level.

At step 402, the cycle times for the various cycles of the test are set. For example, in a three cycle test (e.g., cycles A, B, and C), the operator sets a first time for cycle A by inputting the time on a numeric keypad or other input device and stores this information; the same process is repeated for cycles B and C. Alternatively, if test information is stored for a particular patient in control processor 120, then the operator could input identification information to identify the patient, and the patient's test cycle information could be set from the stored patient data. Obviously, any method of inputting the appropriate cycle times may be utilized and, obviously, while three cycles are given in the above example, any number of cycles may be utilized as long as sufficient fluid is available for use.

At step 404, temperature readings are again taken from all reservoirs to make sure that the temperature is still at the desired level. At step 406, if a determination is made that the temperatures are not appropriate, then at step 408 the heaters 251 are activated where needed until temperature readings indicate that the fluid temperature is stabilized at the desired temperature. Once the reservoirs are at the desired temperature, at step 410, the irrigation nozzle of IDU 110 is inserted into the patient's ear. At step 412, the first cycle is run, e.g., by activating the trigger on the IDU 110. When the trigger is activated, a signal from processor 120 to valve 244 causes valve 244 to open for the time period input for cycle A. At step 414, the second cycle is automatically run when cycle A is completed. This is accomplished by control processor 120 closing valve 244 and opening valve 246 for the appropriate time period for cycle B.

At step 416, the third cycle is run automatically when cycle B has completed. This is accomplished by control processor 120 closing valve 246 and reopening valve 244 for the appropriate time period input for cycle C. In this example, once all three cycles A, B, and C, have been completed, the test is ended.

In view of the flexibility provided by the ability to configure control processor 120 as desired, any of the functions available may be run at any time during the operation. Thus, for example, while FIG. 4 illustrates a basic three cycle test involving a certain series of steps, temperature readings may be taken at timed intervals throughout the test and the heaters may be activated, where necessary, to keep the temperatures at the appropriate levels. Further, sensor data from the point of delivery sensors can be processed and, if the temperature at the point of delivery drops below a particular level, then the point of delivery heaters may be activated to increase the temperature to the appropriate temperature level.

In addition, once the test is ended at step 418, if desired, the statistics received from the ENG sensors can be stored in process controller 120 and conventional computerized analysis processes may be performed on the data and/or any historical data to develop and produce reports on aspects of the test just completed, historical reports showing statistical trends with respect to the patient undergoing the test, and/or, comparative statistical data comparing the test results of the patient under test with other patients' test results.

While there has been described herein the principles of the invention, it is to be understood by those skilled in the art that this description is made only by way of example and not as a limitation to the scope of the invention. For example, while there has been described a two-temperature system in which main reservoir fluids are heated to two higher temperatures for use during irrigation, it is also contemplated that more than two secondary reservoirs may be used, and that the fluid in one or more of the secondary reservoirs may be cooled or used without temperature change, instead of being heated. In addition, while the above description discusses the storage of patient data in the memory of the process controller, it is understood that any storable data, including initialization data, processing data, "instructions" which control the operation of any of the systems of the device, may be captured and/or stored in the memory of the process controller so that any and all operations can be automated. Further, while an ENG sensor is illustrated as an appropriate patient response sensor for use in the present system, other sensors, including EEGs may be used, and multiple sensors (e.g., both an EEG and an ENG) may be utilized as well. Further, it is understood that, based upon the data sensed by the patient response sensors, the process controller can modify the testing process in real-time to, for example, accentuate observed responses. Accordingly, it is intended by the appended claims, to cover all modifications of the invention which fall within the true spirit and scope of the invention.

What is claimed is:

1. An apparatus for irrigating an ear canal of a patient, comprising:
    an irrigation supply unit storing irrigation fluid;
    an irrigation delivery unit coupled to said irrigation supply unit, said irrigation delivery unit delivering said stored irrigation fluid to said ear canal;
    a process controller coupled to said irrigation supply unit, said process controller configured to automatically control the temperature, flow rate, and timing of delivery of said stored irrigation fluid to said ear canal; and
    a patient response sensor coupled to said process controller, said patient response sensor sensing patient's response to said irrigation process and sending response data indicative of said response to said process controller.

2. An apparatus as set forth in claim 1, wherein said process controller comprises a memory, and is configured to store said response data for each patient tested using said apparatus.

3. An apparatus as set forth in claim 2, wherein said process controller is configured to analyze said stored response data and output diagnostic information relating to said stored response data.

4. An apparatus as set forth in claim 2, wherein said process controller is configured to analyze said stored response data and output statistical information relating to said stored response data.

5. An apparatus for irrigating an ear canal of a patient, comprising:
    an irrigation supply unit storing irrigation fluid including:
        a main reservoir for storing a minimum supply of irrigation fluids; and
        a plurality of secondary reservoirs for storing secondary supplies of irrigation fluid supplied from said main reservoir;
    an irrigation delivery unit coupled to said irrigation supply unit, said irrigation delivery unit delivering said stored irrigation fluid to said ear canal;
    a process controller coupled to said irrigation supply unit, said process controller configured to automatically control the temperature, flow rate, and timing of delivery of said stored irrigation fluid to said ear canal, configured to store test parameter data related to said temperature, flow rate and timing control, and configured to store response data for each patient tested using said apparatus; and
    a patient response sensor coupled to said process controller, said patient response sensor sensing a patient's response to said irrigation process and sending response data indicative of said response to said process controller.

6. An apparatus as set forth in claim 5, wherein said test parameter data comprises test parameter data for a plurality of patients to be tested.

7. An apparatus as set forth in claim 6, wherein said process controller is configured to analyze said stored response data and output diagnostic information relating to said stored response data.

8. An apparatus as set forth in claim 7, wherein each of said secondary reservoirs include a respective temperature sensor, each of said temperature sensors supplying temperature data to said process controller for the fluid contained in a respective one of said secondary reservoirs.

9. An apparatus as set forth in claim 8, wherein each of said secondary reservoirs further include a respective heat source, and wherein each of said heat sources are automatically activated by said process controller to heat the fluid contained in said respective secondary reservoirs upon receipt by said process controller of temperature data indicating that the temperature of the fluid in said respective secondary reservoirs has fallen below a predetermined threshold temperature.

* * * * *